United States Patent [19]

Stamler et al.

[11] Patent Number: 5,298,506
[45] Date of Patent: Mar. 29, 1994

[54] USE OF GUANYLATE CYCLASE INHIBITORS IN THE TREATMENT OF SHOCK

[75] Inventors: Jonathan Stamler, Boston; Joseph Loscalzo, Dedham, both of Mass.

[73] Assignee: Brigham and Women's Hospital, Boston, Mass.

[21] Appl. No.: 880,444

[22] Filed: May 8, 1992

[51] Int. Cl.$^5$ .................. A61K 31/07; A61K 31/19; A61K 31/47; A61K 31/54
[52] U.S. Cl. .................. 514/226.2; 514/312; 514/571; 514/667; 514/725
[58] Field of Search .............. 514/226.2, 312, 571, 514/667, 725

[56] References Cited

U.S. PATENT DOCUMENTS 5,002,964  3/1991  Loscalzo .................. 514/423
5,025,001  6/1991  Loscalzo .................. 514/91

OTHER PUBLICATIONS

Kilbourn et al., *Biochem. and Biophys. Res. Comm.* 172(3):1132–1138 (1990).
Petros et al., *Lancet* 338:1557–1558 (1991).
Lamas et al., *Am. J. Physiol.* 261:C634–C641 (1991).
Nava et al., *Lancet* 338:1555–1557 (1991).
Huang et al., *Eur. J. Pharmacol.* 205:289–294 (1991).
Culo et al., *Agents and Actions* 34 (3/4):424–428 (1991).
Kiese et al., *Eur. J. Clin. Pharmacol.* 4:115–118 (1972).
Burrows et al., *Proc. Ann. Meet. US Ani. Health Assoc.* 79:266–270 (1975).
Sloand et al., *Thrombi. Res.* 54:677–686 (1989).
Beasley et al., *J. Clin. Invest.* 87:602–608 (1991).
Marsden et al., *J. Exp. Med.* 172:1843–1852 (1990).
Garthwaite G. et al., *Neuroscience* 26(1):321–326 (1988).
Kashiwabara et al., *Eur. J. of Pharmacol.* 196:1–7 (1991).

*Primary Examiner*—Leonard Schenkman
*Attorney, Agent, or Firm*—Charles J. Herron; Elliot M. Olstein

[57] ABSTRACT

The invention relates to the administration of guanylate cyclase inhibitors, such as methylene blue, for the treatment of septic shock, cardiogenic shock, hypovolemic shock, obstructive shock, neuropathic shock and hypotension caused by excessive doses of nitrovasodilators. The invention also relates to the use of other redox dyes, such as toluidine blue, neutral red, tetrazolium salts, chloranil and dichlorophenolindophenol for the treatment of shock.

10 Claims, 1 Drawing Sheet

USE OF GUANYLATE CYCLASE INHIBITORS IN THE TREATMENT OF SHOCK

BACKGROUND OF THE INVENTION

1. Field of the Invention

The invention relates to a new method for the treatment of shock states, such as septic shock, cardiogenic shock, hypovolemic shock, shock caused by blood flow obstruction, neuropathic shock, and hypotensive disorders, comprising administering a pharmaceutical composition containing a guanylate cyclase inhibitor to a patient.

2. Brief Description of the Background Art

Shock is a clinical emergency, characterized by widespread, serious reduction in tissue perfusion which, if prolonged, leads to generalized impairment of cellular function. Shock is usually associated with systemic hypotension resulting from a significant decrease in either cardiac output or systemic vascular resistance, without a compensatory increase in the other.

Shock states are classified according to the precipitating factors. Examples include septic (bacteremia), cardiogenic (heart pump failure), hypovolemic (fluid loss), obstructive (circulatory obstruction), and neuropathic (drugs or spinal cord injury).

Septic shock, a life-threatening complication of bacteremia affects 150,000 to 300,000 patients annually in the United States, and has a mortality rate of 50% to 75% (Kilbourn et al., *Biochem. and Biophys. Res. Comm.* 172(3):1132–1138 (1990); Petros et al., *The Lancet* 338:1557–1558 (1991)). The shock state is characterized by circulatory insufficiency due to diffuse cell and tissue injury and the pooling of blood in the microcirculation.

The pathogenesis of the cardiovascular collapse that occurs during septic shock is poorly understood, but is believed to occur as a result of the reaction between bacterial products and components of the coagulation and complement systems. For example, bacterial endotoxin activates the synthesis and release of inflammatory mediators such as leukotrienes, prostaglandins, cytokines, such as tumor necrosis factor (TNF), and platelet activating factor. These inflammatory mediators significantly affect vasomotor tone, microvascular permeability and leukocyte and platelet aggregation.

In addition, endotoxin activates the alternative complement pathway, resulting in generation of C3a and C5a, which in turn affect platelet aggregation and vascular tone. Activation of the coagulation system by bacterial products further alters the microcirculation in tissues by contributing to thrombi formation. Finally, endotoxin stimulates release of vasoactive substance such as catecholamines, glucocorticosteroids, histamine and serotonin which, in combination, contribute to the eventual circulatory collapse.

Cardiogenic shock is the most important fatal complication of acute myocardial infarction, occurring in approximately 10% of such patients, and accounting for approximately two-thirds of in-hospital deaths. Other causes of cardiogenic shock include arrhythmias, severe congestive heart failure, mitral valve or aortic valve regurgitation, and perforation of the ventricular septum. The shock state occurs as a consequence of the decrease in arterial pressure and consequent reduction in coronary blood flow, resulting from the significant reduction in the quantity of contracting myocardium. This reduction in blood flow may further impair myocardial function, thereby increasing the size of the infarction.

Both septic and cardiogenic shock have been associated with an increase in the production of nitric oxide or endothelium-derived relaxing factor, (EDRF), a potent labile vasodilator which plays a major role in the regulation of local blood flow, vasomotor tone and systemic blood pressure through activation of soluble guanylate cyclase. In animal models of systemic shock, endotoxin and cytokines, such as interleukin-1 (IL-1) and TNF, have been shown to cause vascular relaxation and hypotension by increasing nitric oxide (NO) synthesis. In septic shock in particular, evidence suggests that TNF stimulates the production of nitric oxide by vascular endothelial cells (Lamas et al., *Am. J. Physiol.* 261(4 Part 1):C634–C641 (1991).

The synthesis of NO from L-arginine, occurs through the action of a constitutive enzyme in the vascular endothelium, which has a role in the physiological control of blood pressure, and an inducible NO synthase expressed throughout vessel walls in response to endotoxin or cytokines (Petros et al., *Lancet* 338:1557–1558 (1991)). Expression of inducible NO synthase leads to production of large quantities of NO and profound vasodilation, which is often refractory to vasoconstrictive agents. The mechanism by which NO causes vasodilation and hypotension is through activation of guanylate cyclase. This results in increased levels of cyclic GMP, which cause relaxation of smooth muscle. Thus, activation of guanylate cyclase is an important intermediary step in the NO-induced shock state.

Successful treatment of shock requires rapid restoration of cardiac output and tissue perfusion. Two groups of drugs which have been used to treat shock are beta-receptor stimulants (notably dopamine) and alpha-receptor blocking agonists (epinephrine and norepinephrine). However, all of these drugs have important disadvantages associated with their use, and in certain patients, may be ineffective in reversing established shock. Vasoconstrictive agents are often ineffective, and in patients with severe peripheral constriction, these agents may further reduce the already impaired tissue perfusion.

Effective therapy of septic shock requires immediate reversal of the cardiovascular collapse initiated by endotoxin. Because this collapse occurs as a result of complex interactions between a number of factors, treatment methods are often partially effective at best.

Recently, endotoxin-binding agents, including polymyxin B and antibodies which neutralize TNF, have been used in an attempt to modify the sequelae of septic shock. While these approaches may have prophylactic value there is no evidence that septic shock can be easily or quickly reversed by endotoxin or TNF removal (Kilbourn et al., supra 1132–1138). Some investigators indicate that NO synthase inhibitors, such as $N^6$-monomethyl-L-arginine (L-NMMA), may be helpful in the treatment of hypotension associated with sepsis or therapeutic use of cytokines, but caution that complete inhibition of endogenous NO synthesis may be counterproductive (Nava et al., *Lancet* 338:1555–1557 (1991)).

Methylene blue, a phenothiazine derivative, is a biological stain of low toxicity, as well as a guanylate cyclase inhibitor (Huang et al., *Eur. J. Pharmacol.* 205:289–294 (1991)). It is a member of a group of compounds, termed "redox dyes", which also includes toluidine blue and neutral red. In mice, methylene blue has been shown to decrease TNF production, when given prior to bacterial lipopolysaccharide challenge (Culo et al., *Agents and Actions* 34(3/4):424-428 (1991)). In addition, methylene blue has been used for the treatment of methemoglobinemia, nitrite intoxication and cyanide poisoning (Kiese et al., *Eur. J. Clin. Pharmacol.* 4:115-118 (1972); Burrows et al., *Proc. Ann. Meet. U.S. Ani. Health Assoc.* 79:266-270 (1975); and Sloand et al., *Thrombi. Res.* 54:677-686 (1989)).

SUMMARY OF THE INVENTION

The invention relates to a method for the treatment of shock states, comprising the administration of a therapeutically effective amount of a guanylate cyclase inhibitor to a patient in need thereof.

The invention also relates to the method of the invention, wherein said guanylate cyclase inhibitor is selected from the group consisting of methylene blue, 6-anilino-5,8-guinalinedione (LY83583), N-methylhydroxylamine, hydroxylamine, ethacrynic acid and retinol.

The invention also relates to the method for treatment of shock, comprising the administration of a therapeutically effective amount of a redox dye to a patient in need thereof.

The invention also relates to the methods of the invention wherein said redox dye is selected from the group consisting of methylene blue, toluidine blue, neutral red, tetrazolium salts, chloranil and dichlorophenolindophenol.

The invention also relates to the methods of the invention, wherein said shock comprises septic shock, cardiogenic shock, hypovolemic shock, shock resulting from blood flow obstruction, neuropathic shock, and hypotensive disorders.

The invention also relates to the methods of the invention wherein said compounds are administered as part of a pharmaceutical composition comprising a pharmaceutically acceptable carrier.

The invention also relates to the methods of the invention wherein said pharmaceutical composition is administered to a patient by a route comprising intravenous, intramuscular, subcutaneous, sublingual, oral, rectal or aerosol delivery.

The invention also relates to the methods of the invention wherein said patient is a human.

Figure 1:
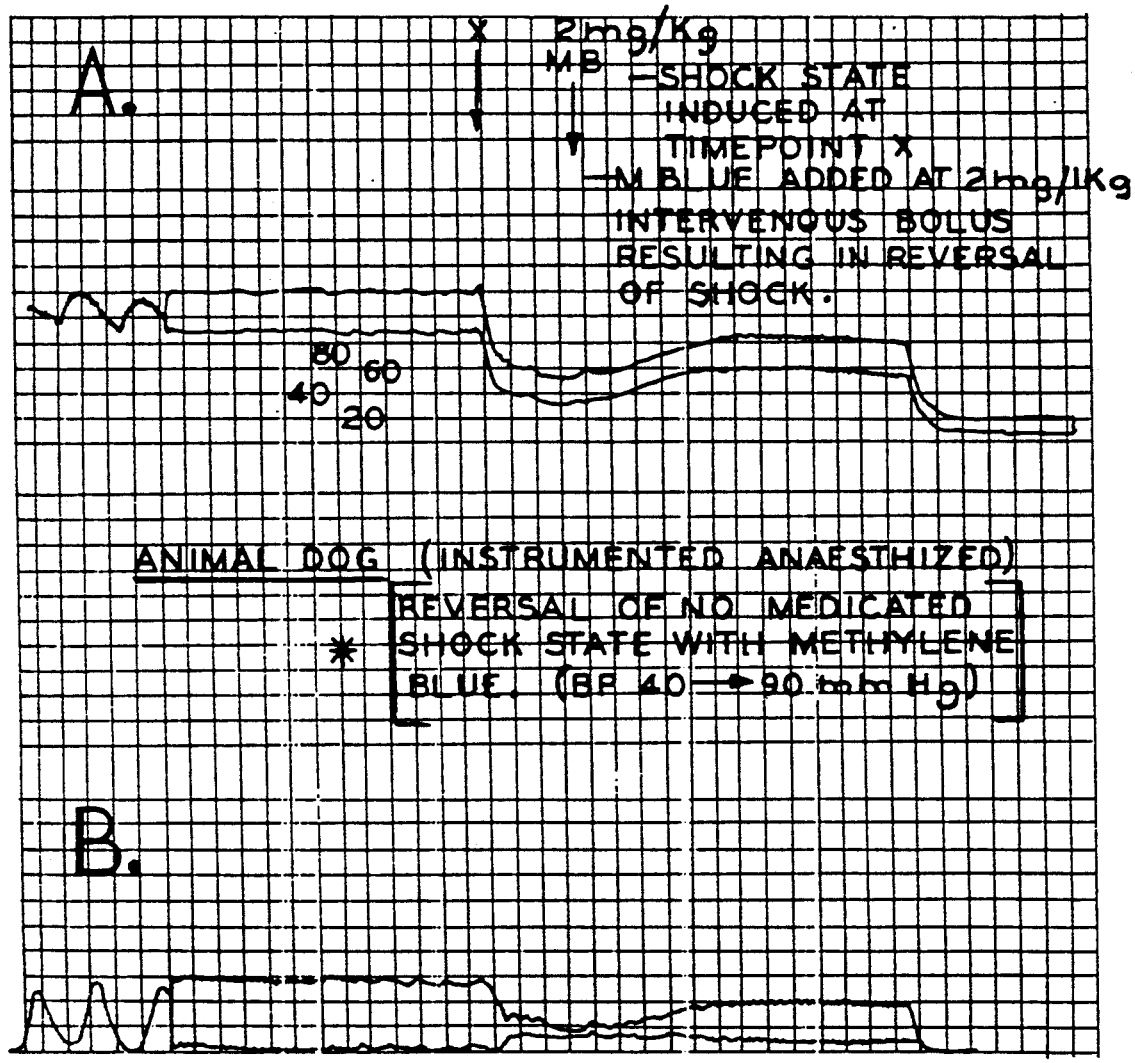
FIG. 1.

A. Increase in systemic arterial pressure (from 40 mmHg to 90 mmHg) following intravenous administration of methylene blue.

B. Systemic arterial pressure remains at 40 mmHg in the absence of administration of methylene blue.

DESCRIPTION OF THE PREFERRED EMBODIMENTS

The invention is related to the discovery that administration of a guanylate cyclase inhibitor to a patient can be used to treat shock.

The term "guanylate cyclase inhibitor" refers to a compound which inhibits the guanylate cyclase-induced formation of the intracellular second messenger, cyclic GMP. Examples of guanylate cyclase inhibitors include, but are not limited to, methylene blue, 6-anilino-5,8-guinalinedione (LY83583), N-methylhydroxylamine, hydroxylamine, ethacrynic acid and retinol. Types of shock include, but are not limited to, septic shock, cardiogenic shock, hypovolemic shock, shock resulting from blood flow obstruction, neuropathic shock, and hypotensive disorders. The term "hypotensive disorders" refers to a decrease in blood pressure resulting from excessive doses of nitrovasodilators, orthostatic hypotension, or any other physiological mechanism.

A particular embodiment of the claimed invention relates to the administration of methylene blue to a patient for the treatment of shock. The inventors have demonstrated, in an in vivo model, that infusion of methylene blue caused an immediate reversal of an induced hypotensive shock state.

While the inventors do not wish to be limited to any particular theory, there are a number of possible mechanisms by which guanylate cyclase inhibitors, such as methylene blue, reverse the actions of nitric oxide and related oxides of nitrogen. Methylene blue generates superoxide, which inactivates NO. Furthermore, methylene blue reacts directly with thiols, which are important in reducing higher oxides with nitrogen, to NO. Methylene blue also interacts directly with vasoactive nitroso-amines which are sources of NO, and may also directly oxidize NO to $NO^+$, which then renders it susceptible to scavenging by a variety of biological molecules. Finally, methylene blue inactivates guanylate cyclase, the enzyme responsible for raising cyclic GMP levels, which is critical, as the cGMP second messenger is central to the hypotensive effect of NO.

In another embodiment of the invention, related redox dyes, including toluidine blue and neutral red, are used to inhibit the effect of NO and related oxides of nitrogen, in shock.

An additional embodiment of the invention relates to the administration of the compounds of the invention as part of a pharmaceutical composition, comprising a pharmaceutically acceptable carrier, to achieve the physiological effects discussed above.

The pharmaceutical compositions utilized in this invention are preferably administered by intravenous means. Alternative routes of administration include, but are not limited to, intramuscular, subcutaneous, sublingual, oral, rectal or aerosol.

The compounds of this invention can be employed in combination with conventional excipients; i.e., pharmaceutically acceptable organic or inorganic carrier substances suitable for parenteral application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

For parenteral application, particularly suitable vehicles consist of solutions, preferably oily or aqueous solutions, as well as suspensions, emulsions, or implants, including suppositories. Ampules are convenient unit dosages.

It will be appreciated that the actually preferred amounts of active compounds used will vary according to the specific compound being utilized, the particular compositions formulated, the mode of application and the particular site of administration. Optimal administration rates for a given protocol of administration can be readily ascertained by those skilled in the art, using conventional dosage determination tests conducted with regard to the foregoing guidelines.

According to the present invention, a "therapeutically effective amount" of a pharmaceutical composition is an amount which is sufficient to achieve the desired pharmacological effect. Generally, the dosage required to provide an effective amount of the composition, and which can be adjusted by one of ordinary skill in the art, will vary, depending upon the age, health, physical condition, sex, weight and extent of the shock state, of the recipient. Additionally, the dosage may be determined by the frequency of treatment and the nature and scope of the desired effect.

Without further elaboration, it is believed that one skilled in the art can, using the preceding description, utilize the present invention to its fullest extent. The following examples are, therefore, to be construed as merely illustrative, and not limitative of the remainder of the disclosure in any way whatsoever.

The entire text of all publications cited above and below are hereby incorporated by reference.

EXAMPLES

Example 1

Reversal of An Induced Shock State By The Administration Of Methylene Blue

An animal study was conducted to test the ability of methylene blue to reverse an induced nitric oxide-mediated shock state. The study was carried out in a dog which was anesthetized with sodium pentobarbital, orotracheally intubated and ventilated, and catheterized to achieve femoral arterial access.

S-nitroso-bovine serum albumin (S-NO-BSA), a molecule which releases bioactive nitric oxide in vivo, was synthesized by incubating BSA (200 mg/ml.) with nitric oxide generated from equimolar $NaNO_2$ in 0.5N HCl for thirty minutes at room temperature. After anesthesia of the animal was achieved, the shock state was induced by administration of S-NO-BSA, (concentration of 50 $\mu M$), by intravenous bolus, which decreased systemic arterial pressure to 40 mmHg, within one minute following administration. Methylene blue (at 2 mg/kg) was then administered by intravenous bolus. Immediately following administration of methylene blue, the systemic arterial pressure increased from 40 to 90 mmHg. The time interval from induction of the shock state, through its reversal, lasted approximately two minutes.

As shown in FIG. 1A, administration of methylene blue caused immediate reversal of an induced nitric oxide-mediated shock state. In contrast, in the absence of methylene blue administration, systemic arterial pressure remained at 40 mmHg (as shown in FIG. 1B).

What is claimed:

1. A method for the treatment of shock, comprising the administration of a therapeutically effective amount of a guanylate cyclase inhibitor to a human patient in need thereof.

2. The method of claim 1 wherein said guanylate cyclase inhibitor is selected from the group consisting of methylene blue, 6-anilino-5, 8-quinolinedione, N-methylhydroxylamine, hydroxylamine, ethacrynic acid and retinol.

3. The method of claim 1 wherein said shock comprises septic shock, cardiogenic shock, hypovolemic shock, shock resulting from blood flow obstruction, neuropathic shock, and hypotensive disorders.

4. The method of claim 1, wherein said compound is administered as part of a pharmaceutical composition comprising a pharmaceutically acceptable carrier.

5. The method of claim 4, wherein said pharmaceutical composition is administered to a patient by a route comprising intravenous, intramuscular, subcutaneous, sublingual, oral, rectal or aerosol delivery.

6. A method for the treatment of shock, comprising the administration of a therapeutically effective amount of a redox dye to a human patient in need thereof.

7. The method of claim 6, wherein said redox dye is selected from the group consisting of methylene blue, toluidine blue and neutral red, tetrazolium salts, chloranil, and dichlorophenol-indophenol.

8. The method of claim 6 wherein said shock comprises septic shock, cardiogenic shock, hypovolemic shock, shock resulting from blood flow obstruction, neuropathic shock, and hypotensive disorders.

9. The method of claim 6 wherein said compound is administered as part of a pharmaceutical composition comprising a pharmaceutically acceptable carrier.

10. The method of claim 9 wherein said pharmaceutical composition is administered to a patient by a route comprising intravenous, intramuscular, subcutaneous, sublingual, oral, rectal or aerosol delivery.

* * * * *